(12) United States Patent  (10) Patent No.: US 9,008,748 B2
Su et al.  (45) Date of Patent: Apr. 14, 2015

(54) WATERPROOF PHYSIOLOGICAL SIGNAL DETECTION DEVICE

(75) Inventors: I-Chen Su, Taipei (TW); Hong-Hsu Huang, Taipei (TW); Shun-Tung Yang, Taipei (TW)

(73) Assignee: King's Metal Fiber Technologies Co., Ltd., Taichung (TW)

( * ) Notice: Subject to any disclaimer, the term of this patent is extended or adjusted under 35 U.S.C. 154(b) by 462 days.

(21) Appl. No.: 13/562,367

(22) Filed: Jul. 31, 2012

(65) Prior Publication Data

US 2014/0039292 A1 Feb. 6, 2014

(51) Int. Cl.
 *A61B 5/04* (2006.01)
 *A61B 5/0408* (2006.01)
 *A61B 5/0424* (2006.01)
 *A61B 5/0478* (2006.01)
 *A61B 5/00* (2006.01)

(52) U.S. Cl.
 CPC .......... *A61B 5/0408* (2013.01); *A61B 5/04087* (2013.01); *A61B 5/0424* (2013.01); *A61B 5/0478* (2013.01); *A61B 5/6832* (2013.01); *A61B 2562/14* (2013.01); *A61B 2562/168* (2013.01)

(58) Field of Classification Search
 CPC .. A61B 5/6804; A61B 5/6805; A61B 5/0006; A61B 5/6831; A61B 5/0402; A61N 1/0484; A61N 1/0492; A61N 1/22; A61N 1/321

USPC ......... 600/372, 382, 384, 386, 388–391, 393, 600/395, 397, 508–509
 See application file for complete search history.

(56) References Cited

U.S. PATENT DOCUMENTS

| | | | | |
|---|---|---|---|---|
| 3,534,727 | A | * | 10/1970 | Roman .......................... 600/389 |
| 6,065,154 | A | * | 5/2000 | Hulings et al. .................... 2/102 |
| 2003/0212319 | A1 | * | 11/2003 | Magill .......................... 600/382 |
| 2004/0073104 | A1 | * | 4/2004 | Brun del Re et al. .......... 600/372 |
| 2007/0073131 | A1 | * | 3/2007 | Ryu et al. ....................... 600/388 |
| 2009/0227856 | A1 | * | 9/2009 | Russell et al. ................. 600/388 |
| 2010/0191090 | A1 | * | 7/2010 | Shin et al. ...................... 600/388 |
| 2010/0317954 | A1 | * | 12/2010 | Jeong et al. .................... 600/372 |

* cited by examiner

*Primary Examiner* — Joseph Stoklosa
*Assistant Examiner* — Brian M Antiskay
(74) *Attorney, Agent, or Firm* — Bacon & Thomas, PLLC

(57) ABSTRACT

A waterproof physiological signal detection device includes at least one electrode pad, a waterproof base layer, at least one water absorption unit, and a waterproof top layer. The electrode pad is positioned on a top surface of the waterproof base layer, and a first receiving compartment formed therebetween. The water absorption unit is positioned in the first receiving compartment. The water absorption unit has a top engaging the electrode pad and s a bottom engaging the waterproof base layer. The waterproof top layer overlaps the waterproof base layer and forms at least one top layer opening that corresponds to and exposes the at least one electrode pad. An undersurface of a circumference of the top layer opening overlaps a circumference of a top surface of the electrode pad with a central portion of the electrode pad projecting through the top layer opening.

22 Claims, 14 Drawing Sheets

WATERPROOF PHYSIOLOGICAL SIGNAL DETECTION DEVICE

FIELD OF THE INVENTION

The present invention relates to a waterproof physiological signal detection device, and in particular to a physiological signal detection device that provides water-absorbing, water-resistance, and wet-keeping functions to wet an electrode pad for engagement with a surface of human body in order to facilitate conductive performance for detecting physiological signal and be applicable to detection of physiological signals of human body in a dry area.

BACKGROUND OF THE INVENTION

Nowadays, to detect physiological signals of human body, such as heart beat and brain wave, a plurality of electrode pads of physiological detection equipment is attached to (or worn on) various sites on a surface of human body (also referred to as body surface). These electrode pads detect the current that spreads to the peripheral tissues or body surface occurring when nervous impulses (namely variation of membrane potential) passes through human body organs (such as heart and head). The current is then transmitted by electrical wires to the physiological detection equipment to be converted into data to be displayed. In this way, the condition of an inspected portion (such as heart rate and variation of brain wave) can be realized.

The conventional electrode pad has a structure comprising a base layer (such as a layer of conductive adhesive) and an electrically conductive portion bonded to the base layer. To use in inspecting physiological signals, the body surface (such as skin) is made wet by the stickiness of the base layer or through additional application of a layer of aqueous gel that is electrically conductive in order to help the current on the body surface to flow through the base layer, the electrically conductive portion, and the electrical wires to the physiological detection equipment. On the other hand, to carry out electrotherapy, electrical current is transmitted from the physiological detection equipment to the body surface to penetrate into the body surface to simulate the portion to be treated.

However, the base layer of the conventional electrode pad, as well as the aqueous gel used in combination therewith, is generally not air permeable and may often cause allergy, and thus resulting in uncomfortableness of use. Further, skin chips (for example in condition of dry skin) and grease (in condition of oily skin) are often generated on the human body surface and may easily get stuck to the base layer and interferes with conduction of electrical current. Further, human body has body temperature, which may often causes loss (evaporation) of body surface humidity, or the gel used may get dried and is no longer capable of a humid condition, leading to separation of the adhesive from the base layer. This also interferes with the conduction of electrical current and makes it hard to detect physiological signals. Particularly in a dry condition, the humidity is even harder to keep and interruption of detection results. It may also cause cracking of the base layer.

Further, when multiple conventional electrode pads are used, if these conventional electrode pads are placed too close to each other, then they may get contact with each other and short-circuit may result.

In view of these problems, the present invention aims to provide a physiological signal detection device that provides water-absorbing, water resistance, and wet-keeping functions to improve electrical conduction for physiological signal detection and to facilitate use in a dry area to detect physiological signals of an inspection subject and to increase the convenience of use.

SUMMARY OF THE INVENTION

An object of the present invention is to provide an improved physiological signal detection device that provides water-absorbing, water resistance, and wet-keeping functions to improve electrical conduction for physiological signal detection and facilitate use in a dry area to detect physiological signals of an inspection subject and to increase the convenience of use.

Another object of the present invention is to provide a physiological signal detection device that comprises a thermoplastic bonding layer and shows water resistance so as to facilitate use through easy bonding and also provide a function of positioning and thus reduce the influence thereof to the conduction of electrical current.

A further object of the present invention is to provide a physiological signal detection device that forms distinct projections after absorbing water and features water resistance so as to easily attach to and securely bond to human body surface.

To realize the above objects, the present invention provides a waterproof physiological signal detection device that comprises a waterproof base layer; at least one electrode pad, which is positioned on a top surface of the waterproof base layer, the at least one electrode pad and the waterproof base layer forming a first receiving compartment therebetween; at least one water absorption unit, which is positioned in the first receiving compartment, the water absorption unit having a top engaging the electrode pad, the water absorption unit having a bottom engaging the waterproof base layer; and a waterproof top layer, which is positioned to overlap the top surface of the waterproof base layer, the waterproof top layer forming at least one top layer opening, the at least one top layer opening corresponding to and exposing the at least one electrode pad, an undersurface of a circumference of the top layer opening overlapping a circumference of a top surface of the electrode pad, the electrode pad having a central portion projecting through the top layer opening. As such, water absorbing, water resistance, and wet keeping functions are achieved, by which fast loss of water is prevented and additionally, invasion of external liquid that affects the conductivity of electrical current is prevented to reduce noise interference and facilitate wetting of the electrode pad. Further, the water absorption unit is capable of bulging by absorbing water to raise the electrode pad, so that the electrode pad is capable of easy contact and tight engagement with human body surface to ease the detection of physiological signal of an inspection subject and improve convenience of use. Further, thermoplastic bonding layers (such as first and second bonding layers) are additionally included to make bonding easy and realize positioning so as to facilitate alignment of the water absorption unit with respect to the electrode pad, avoiding sliding and thus affecting the performance of conduction of electrical current.

BRIEF DESCRIPTION OF THE DRAWINGS

The present invention will be apparent to those skilled in the art by reading the following description of preferred embodiments thereof with reference to the drawings, in which.

DETAILED DESCRIPTION OF THE PREFERRED EMBODIMENTS

Figure 1:
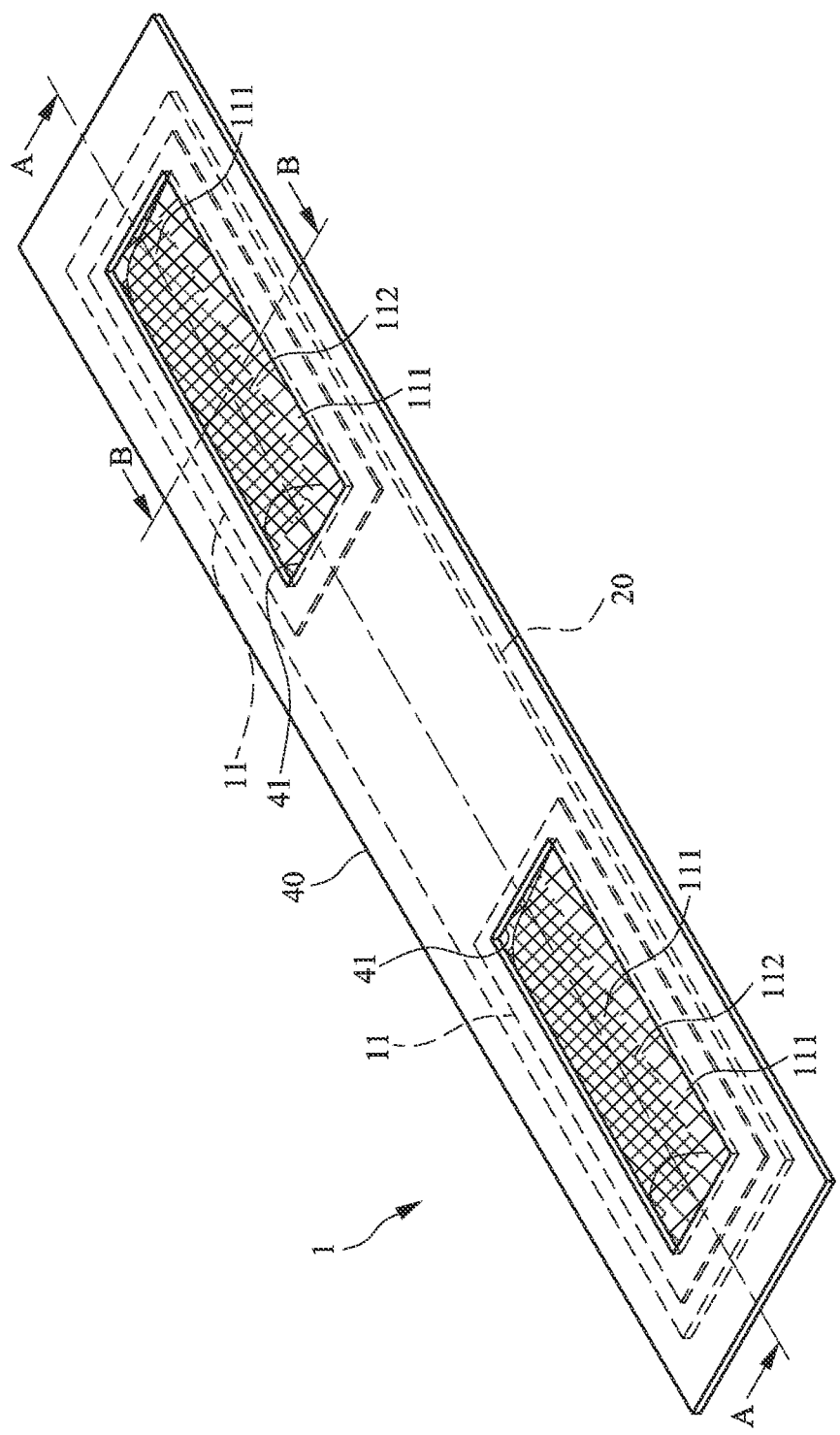
FIG. 1 is a perspective view showing a physiological signal detection device according to the present invention.

With reference to the drawings and in particular to FIGS. 1-13, a waterproof physiological signal detection device 1 according to the present invention comprises a combination of at least one electrode pad 11, a waterproof base layer 20, at least one water absorption unit 30, and at least one waterproof top layer 40. The electrode pad 11 functions to set in contact with a surface of a portion of human body to be inspected. The water absorption unit 30 is arranged to correspond to the electrode pad 11. The waterproof base layer 20 mates and is connected to the waterproof top layer 40 in such a way that only a central portion of the electrode pad 11 is exposed through the waterproof top layer 40. When the mated and connected waterproof base layer 20 and the waterproof top layer 40 are of such structures that shows corresponding size and shape (see FIG. 6), the waterproof base layer 20 can be directly attached to a wearable article (such as garment 50 of FIG. 14), but is not limited to such an arrangement. The present invention also provides that the waterproof top layer 40 can be of a size that is greater than that of the waterproof base layer 20 (see FIG. 1) so that a circumference of the waterproof top layer 40 can be directly attached to the wearable article.

Figure 6:
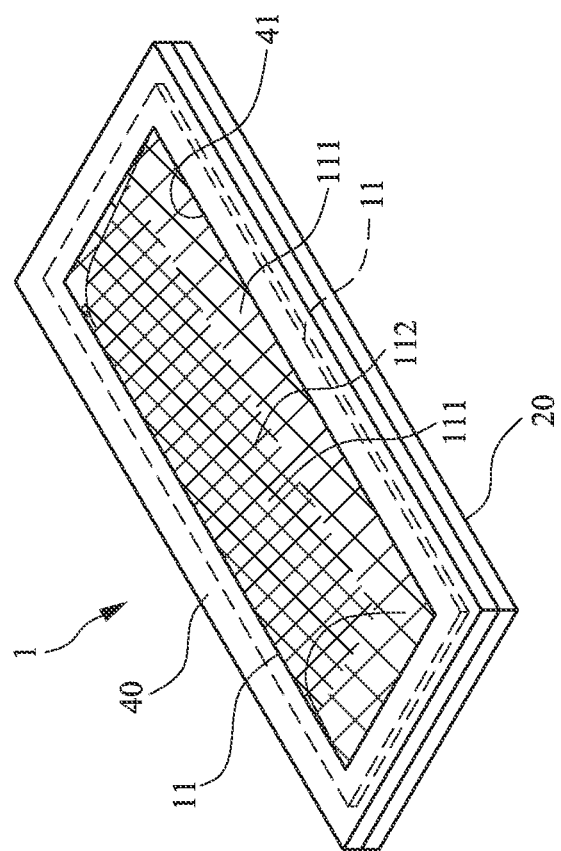
FIG. 6 is a schematic view showing a simple structure of the physiological signal detection device according to the present invention.
Figure 7:
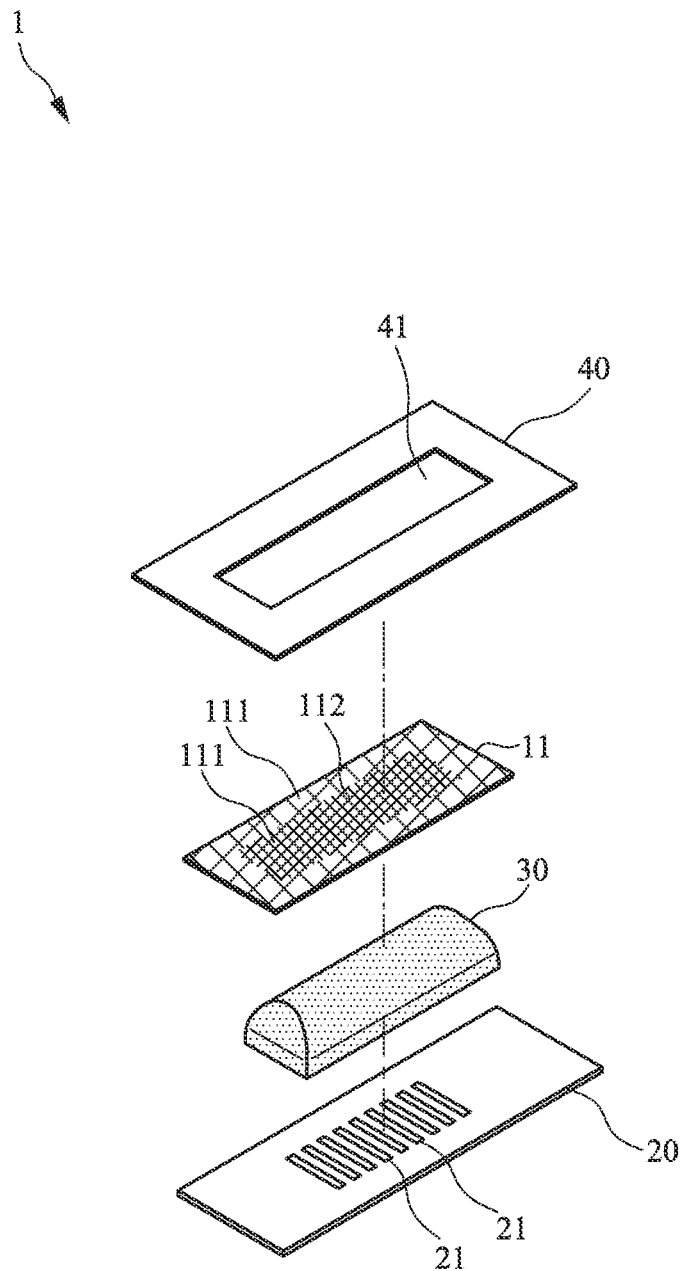
FIG. 7 is an exploded view of FIG. 6.

The physiological signal detection device 1 according to the present invention has a simple structure, which as illustrated in FIGS. 6 and 7, is embodied in the form of a single electrode pad 11. The electrode pad 11 is positioned on a top surface of the waterproof base layer 20 in such a way that the at least one electrode pad 11 and the base layer 20 form therebetween a first receiving compartment S1. The water absorption unit 30 is positioned in the first receiving compartment S1. The water absorption unit 30 has a top engaging the electrode pad 11 and a bottom engaging the waterproof base layer 20. Further, the waterproof top layer 40 is set overlapping a top surface of the waterproof base layer 20 and the waterproof top layer 40 forms at least one top layer opening 41. The at least one top layer opening 41 corresponds to and exposes the at least one electrode pad 11. The undersurface of a circumference of the top layer opening 41 overlaps a circumference of the top of the electrode pad 11 with the central portion of the electrode pad 11 projecting through the top layer opening 41.

With such an arrangement, besides water absorption, the present invention provides also the functions of water resistance and wet keeping, whereby water that provides electrical conductivity is only allowed to enter the physiological signal detection device 1 through the central portion of the electrode pad 11 to be absorbed and preserved in the water absorption unit 30 for subsequent release also through the central portion of the electrode pad 11. This helps wetting the electrode pad 11 with the water absorption unit 30, delays the fast evaporation of water contained in the physiological signal detection device 1, and prevents other liquids (such as oil) from invasion into the physiological signal detection device 1 to thereby affect the performance of electrical conduction.

Figure 14:
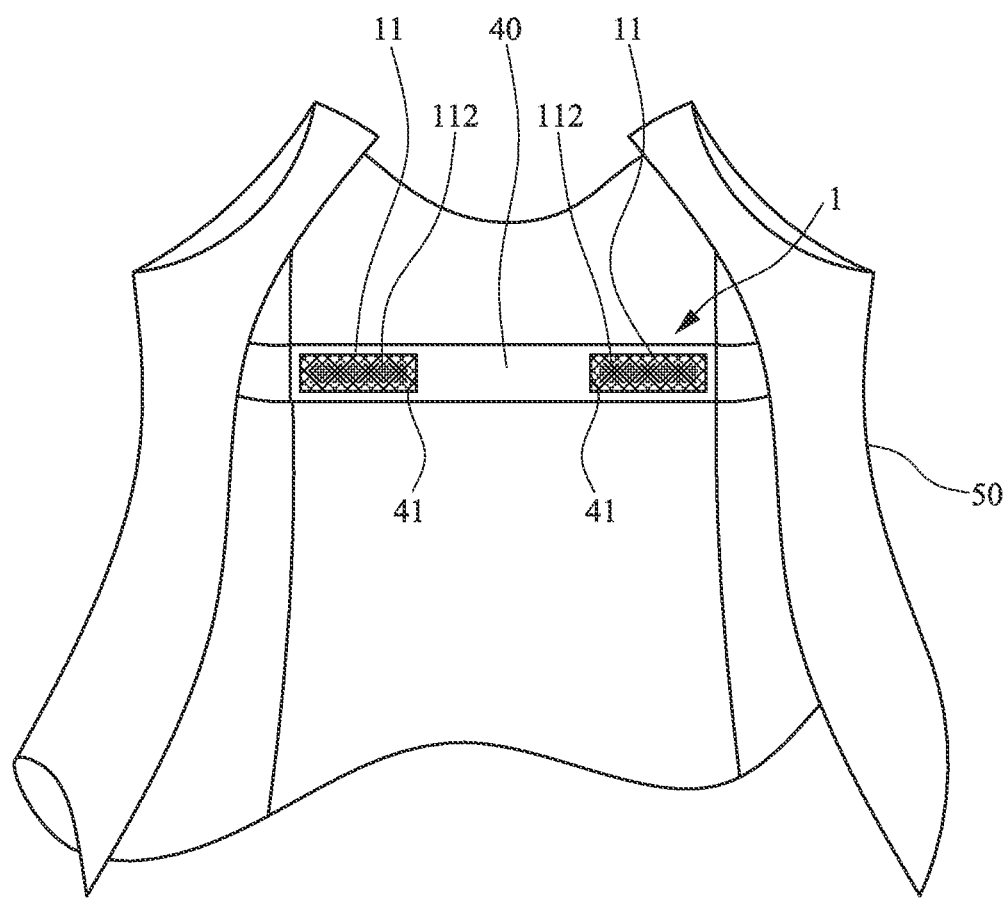
FIG. 14 is a front view showing the physiological signal detection device according to the present invention coupled to a front-open garment.

To actually practice the present invention, the physiological signal detection device 1 according to the present invention can be embodied in various formed according the number of electrode pads 11 used. For an embodiment in which the present invention is embodied with a single electrode pad 11, a wearable article (such as a wrist band or a wrist protector, not shown) with which the physiological signal detection device 1 according to the present invention is combined, is worn on a wrist of a human body (not shown), and an electronic device (such as a multimedia playing device, not shown) is also included, with an opposite end of the electronic device being electrically connected to an accessory (such as an earphone, not shown) that is attached to another portion of human body (such as an ear) for grounding (or negative electric pole) purposes so as to form a detection circuit. For an embodiment in which the present invention is embodied with a plurality of electrode pads 11, the physiological signal detection device 1 of the present invention is not limited to being mounted to wrist and may, as shown in FIG. 14, be coupled to a garment 50 in such a way that two electrode pads 11 that are mounted inside the garment 50 form a detection circuit.

The electrode pad 11 is formed by weaving a plurality of non-conductive fibrous yarns and a plurality of conductive fibrous yarns. The plurality of non-conductive fibrous yarns and the plurality of conductive fibrous yarns are interwoven to form therebetween a plurality of mesh pores 111. The plurality of conductive fibrous yarns of the electrode pad 11 is woven to form a conductive zone 112 that is located at the central portion of the electrode pad 11 to allow of easy contact with the surface of the portion of human body to be inspected. The electrode pad 11 uses the plurality of mesh pores 111 to facilitate penetration of conductive substance (such as water and normal saline) in order to improve conduction of electrical current and also to block foreign objects, such as dusts, from penetrating into the electrode pad 11 for easing subsequent cleaning operation (removing the foreign objects) and maintenance and reducing interference with the conductive zone 112 and minimizing generation of noise and facilitating the water absorption unit 30 absorbing penetrating water to also achieve the function of wet keeping. In the embodiment, the electrode pad 11 is entirely made by weaving a plurality of conductive fibrous yarns to make the entire electrode pad 11 conductive thereby increasing contact area and improving the use for detection.

Figure 2:
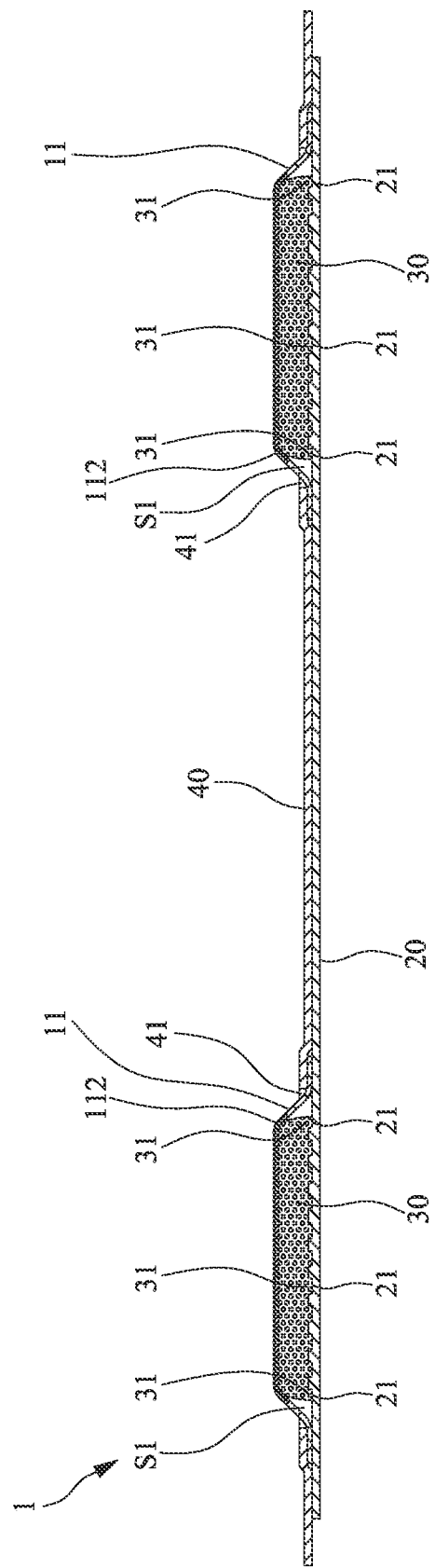
FIG. 2 is a cross-sectional view taken along line A-A of FIG. 1.
Figure 3:
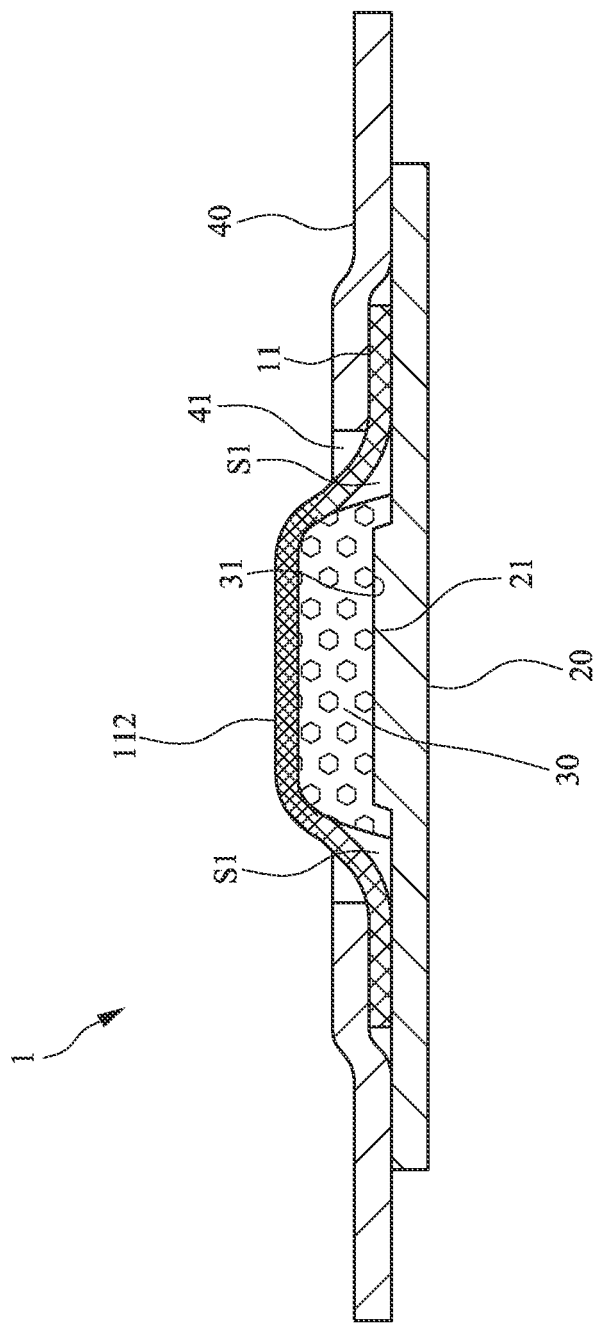
FIG. 3 is a cross-sectional view, in an enlarged form, taken along line B-B of FIG. 1.

To confine the water absorption unit 30 within the first receiving compartment S1 in order to make the water absorption unit 30 corresponding to and uniformly engaging and thus wetting the electrode pad 11, as shown in FIGS. 2 and 3, the water absorption unit 30 forms in a bottom thereof a plurality of spaced anti-skidding sections 31 (such as ribs or grooves). The waterproof base layer 20 forms, in the top surface thereof, a plurality of spaced counterpart anti-skidding sections 21 (such as grooves or ribs). The counterpart anti-skidding sections 21 respectively correspond to the anti-skidding sections 31. The counterpart anti-skidding sections 21 are respectively engageable with the anti-skidding sections 31 in order to make each water absorption unit 30 stably standing in each first receiving compartment S1 and prevent uneven raised configuration on an outside surface of the electrode pad 11 due to sliding of the water absorption unit 30. In an actual way of practicing the present invention, the counterpart anti-skidding sections 21 can be ribs, while the anti-skidding sections 31 are grooves that are engageable with the ribs.

The water absorption unit 30 is a component made of cotton paper, cotton fabric, silica gel, water-absorbing foam, fluff paste (such as pulp), sodium polyacrylate, or other polymers of propenoic acid that show an equivalent function, or can be embodied as a member of superabsorbent polymers showing an equivalent function. In manufacture, the types used can be increased for easy replacement and avoiding unnecessary constraint to a single type of material.

The water absorption unit 30 is an elastic body having a shape that follows an actual manufacturing process to be a sphere (or a block) for easy manufacturing and to make the water absorption unit 30 of the present invention showing elasticity to be expandable or compressible for easy bending or folding and to resume the original shape thereafter so as to easily comply with the curve of surface of human body when attached to the surface of human body thereby facilitating easy use and replacement.

The waterproof base layer 20 and the waterproof top layer 40 can be of a sheet like structure made of thermoplastic material or non-thermoplastic material (such as thermosetting polymer together with fabrics, such as woven fabric, knitting fabric, and non-woven fabric). In a practical embodiment, the waterproof base layer 20 can be a polyvinylchloride (PVC) sheet, a polyurethane (PU) sheet, or a sheet like structure made by weaving other polyester fibers, whereby after being heated, the top surface of the waterproof base layer 20 and the bottom surface of the waterproof top layer 40 can be tightly bonded to each other or alternatively the bottom surface of the waterproof base layer 20 can be directly mounted to a wearable article to prevent the water (or humidity) for electrical conduction from escaping out of the waterproof base layer 20 and also to prevent sideway leakage, so that water (humidity) that enters through the central portion of the electrode pad 11 is prevented from being easily lost through evaporation and can be re-absorbed by the water absorption unit 30 to keep wetting each electrode pad 11 for providing an extended period of time for conduction of electrical current therethrough. In this way, water (or humidity) is prevented from easily draining out of the physiological signal detection device 1 and thus a function of water resistance and wet keeping can be realized.

Figure 4:
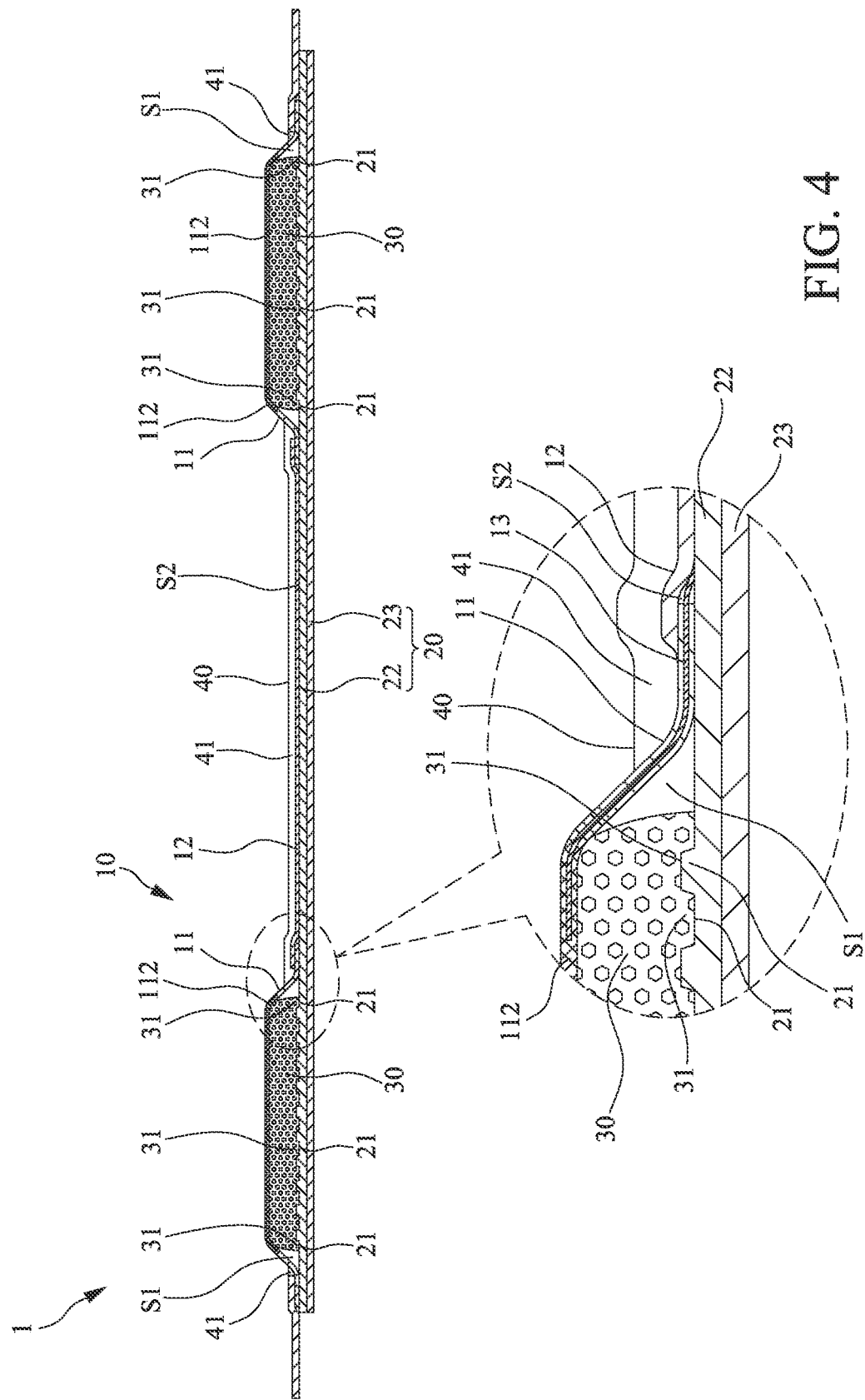
FIG. 4 is a schematic view showing that the physiological signal detection device of FIG. 2 is made in such a way that a waterproof top layer has a single top layer opening, each electrode pad is provided with an extension conductor, a waterproof connection band is connected between the electrode pads, and a waterproof base layer is formed of a water-resistant upper layer and a fabric lower layer overlapping each other.
Figure 8:
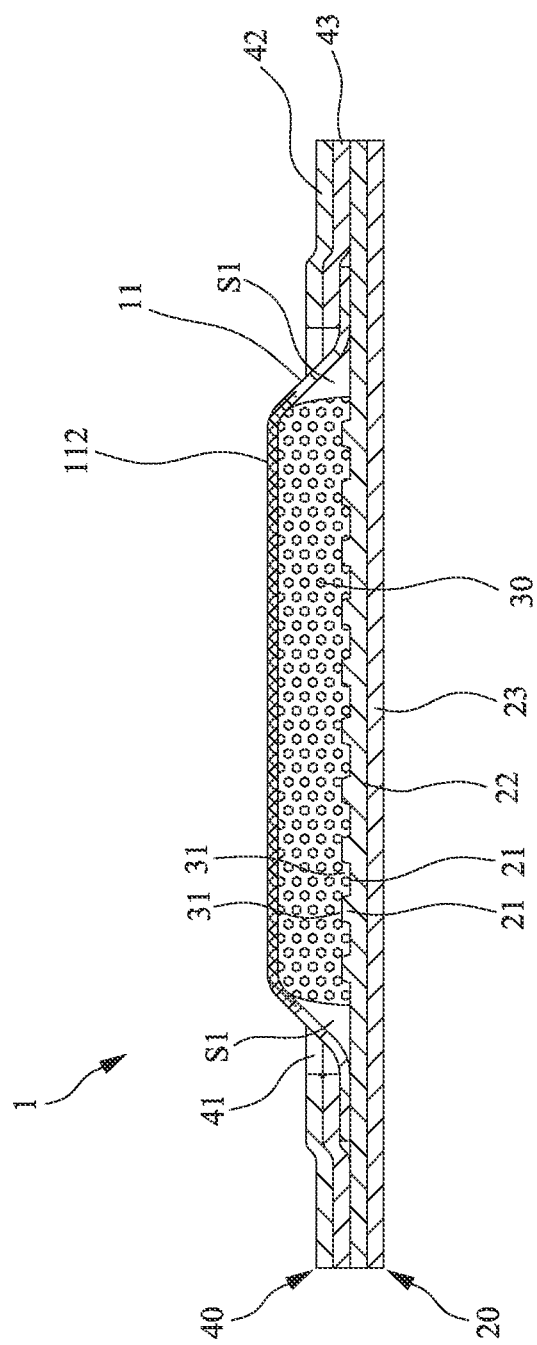
FIG. 8 is a cross-sectional view showing that the physiological signal detection device of FIG. 6 comprises a waterproof base layer that comprises a water-resistant upper layer and fabric lower layer overlapping each other and a waterproof top layer comprises a fabric upper layer and a water-resistant lower layer overlapping each other.

The waterproof base layer 20 of the present invention is not limited to such an arrangement. As shown in FIGS. 4 and 8, the waterproof base layer 20 comprises a water-resistant upper layer 22 and a fabric lower layer 23 overlapping each other. The water-resistant upper layer 22 (such as being made of polyester fibers) is set in contact with each water absorption unit 30 to provide a water resistance function. The fabric lower layer 23 protects the water-resistant upper layer 22. The water-resistant upper layer 22 has a top surface that selectively forms the plurality of counterpart anti-skidding sections 21 that is discussed previously. The fabric lower layer 23 can be mounted to a garment. As shown in FIG. 8, the waterproof top layer 40 of the present invention may be structured to comprise a fabric upper layer 42 and a water-resistant lower layer 43 overlapping each other. The top layer opening 41 penetrates through both the fabric upper layer 42 and the water-resistant lower layer 43 to expose the electrode pad 11. The water-resistant lower layer 43 is set on the top surface of the waterproof base layer 20. The fabric upper layer 42 protects the water-resistant lower layer 43 and also makes the waterproof top layer 40 showing a comfortable, thin and light-weighted, and soft sense of touch to facilitate physical contact with the surface of human body. The water-resistant lower layer 43 of the waterproof top layer 40 can be of a sheet like structure hot pressed onto the fabric upper layer 42 or alternatively be formed through coating. The water-resistant upper layer 22 of the waterproof base layer 20 can also be formed through coating to overlap the fabric lower layer 23.

Figure 9:
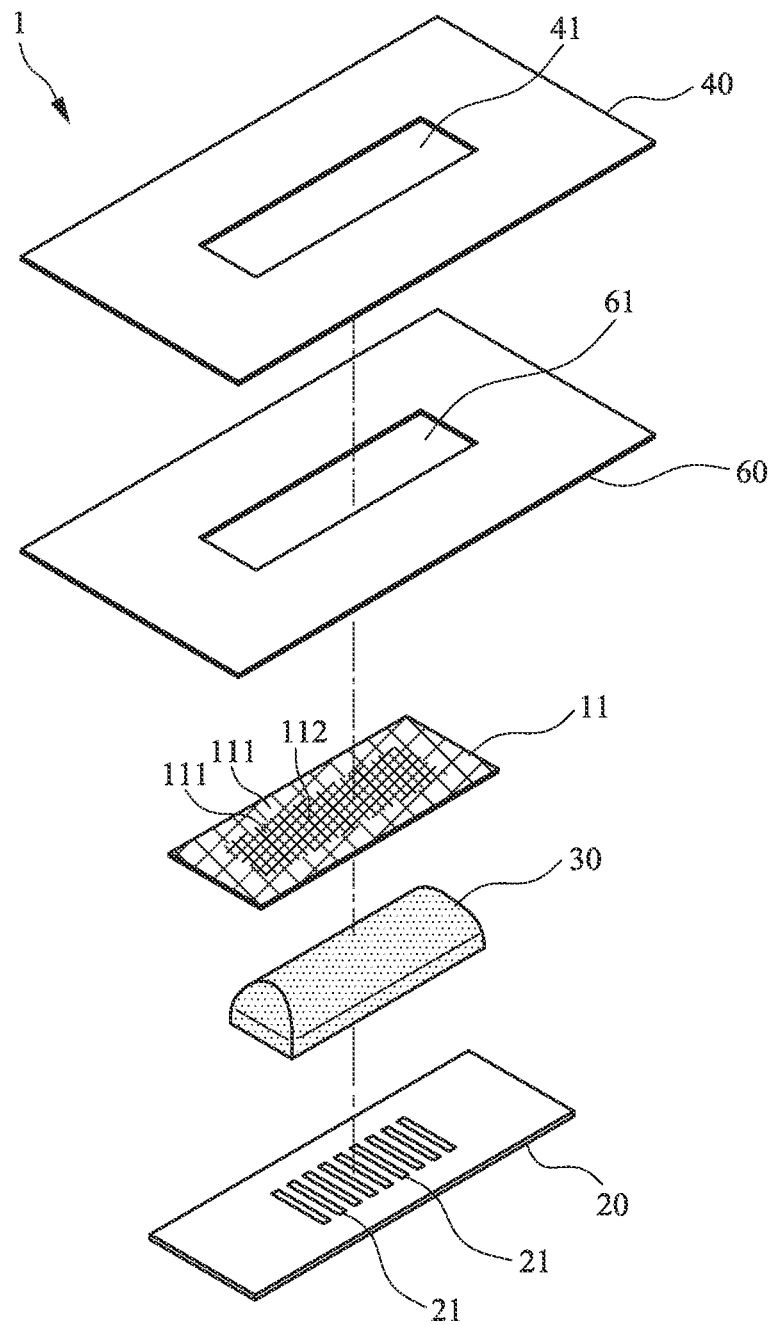
FIG. 9 is an exploded view showing that the physiological signal detection device of FIG. 7 comprises a waterproof top layer that is greater than a waterproof base layer and further comprises a first bonding layer.
Figure 10:
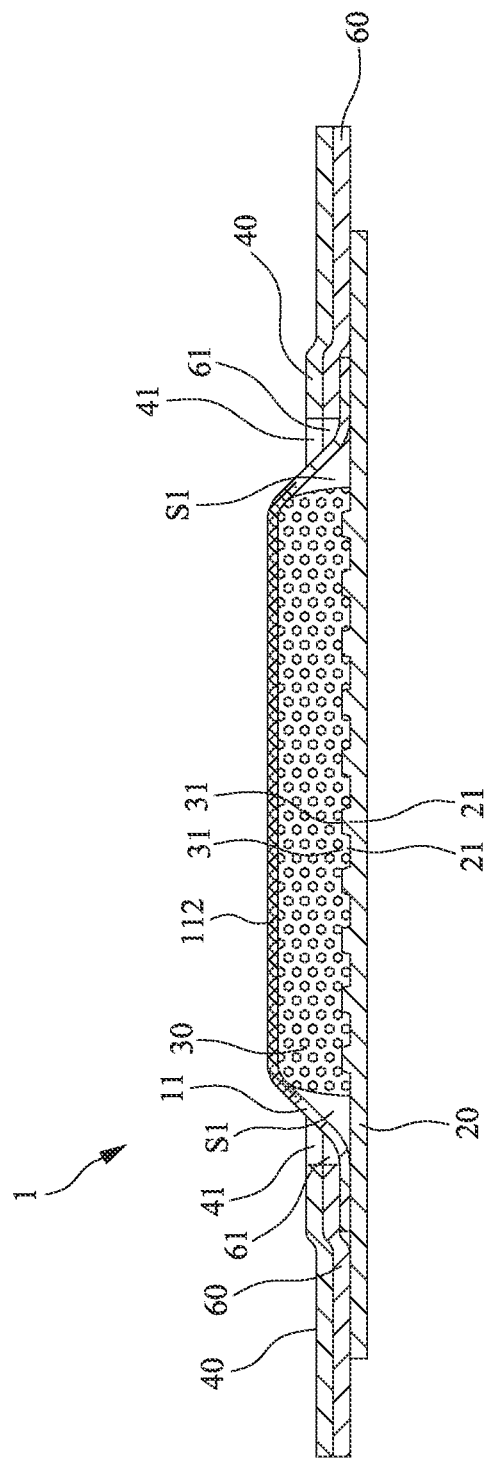
FIG. 10 is a cross-sectional view showing the physiological signal detection device of FIG. 9 after being assembled.
Figure 11:
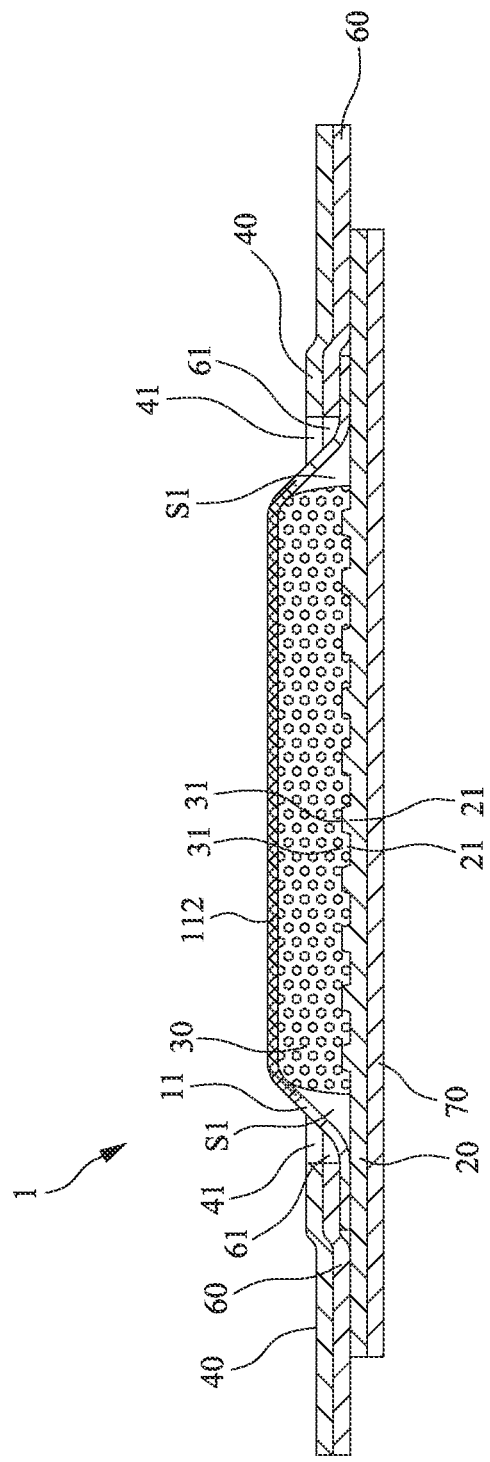
FIG. 11 is a cross-sectional view showing that the physiological signal detection device of FIG. 10 further comprises a second bonding layer 70.

When both the waterproof base layer 20 and the waterproof top layer 40 are not made of a non-thermoplastic material, as shown in FIGS. 9 and 10, the present invention may further comprise a first bonding layer 60, which can be made of hot melt glue or adhesive applied through coating or can be thermoplastic polyurethane (TPU) film. The first bonding layer 60 is set overlapping the bottom surface of the waterproof top layer 40 and the first bonding layer 60 forms at least one bonding layer opening 61. The at least one bonding layer opening 61 corresponds to the at least one top layer opening 41. The undersurface of a circumference of the bonding layer opening 61 corresponds to and overlaps a circumference of a top surface of the electrode pad 11. The central portion of the electrode pad 11 projects through the bonding layer opening 61 and the top layer opening 41. With such an arrangement, after being properly heated, the waterproof base layer 20 and the waterproof top layer 40 are tightly bonded to each other and the electrode pad 11 is positioned on the top surface of the waterproof base layer 20. Further, when the present invention is to be mounted to a garment, since the bonding layer opening 61 can be made in a size greater than the size of the waterproof top layer 40, with the waterproof top layer 40 being made larger than the waterproof base layer 20 (see FIG. 10), the first bonding layer 60 that is exposed at a circumference of the undersurface of the waterproof top layer 40 can be directly bonded to the garment. With such an arrangement, after being properly heated, the physiological signal detection device 1 according to the present invention can be bonded to the garment. If the waterproof top layer 40 and the waterproof base layer 20 are of the same size, then as shown in FIG. 11, the present invention may further comprise a second bonding layer 70, which is made of the same material as the first bonding layer 60 (such as hot melt glue, adhesive, or adhesive tape) in the same way. The second bonding layer 70 is set overlapping the bottom surface of the waterproof base layer 20 so that the second bonding layer 70 can be directly bonded to the garment. With such an arrangement, after being properly heated, the physiological signal detection device 1 according to the present invention can be bonded to the garment 50 (see FIG. 14), whereby after being worn by a subject to be inspected, the conductive zones 112 of the two electrode pads 11 can be tightly attached to a portion to be inspected in an efficient and easy way and individually attaching the pads is not necessary.

Further, herein, the at least one electrode pad 11 can be a plurality of electrode pads 11, and the at least one water absorption unit 30 can be a plurality of water absorption units 30. The term "a plurality of" refers to a number that is equal to or greater than two. A preferred example of the present invention shown in FIGS. 1-3 comprises two electrode pads 11 used in combination with two water absorption units 30. The two electrode pads 11 are arranged, in a mutually spaced manner, on the top surface of the base layer 20 (see FIG. 2) in such a way that each of the electrode pads 11 forms a first receiving compartment S1 with respect to the base layer 20 and the water absorption units 30 are respectively received and retained in the first receiving compartments S1. Each of the water absorption units 30 has a top in engagement with each of the electrode pads 11. Each of the water absorption units 30 has a bottom that is set in engagement with the waterproof base layer 20 to facilitate each of the water absorption units 30 to wet each of the electrode pads 11. The top layer opening 41 of the waterproof top layer 40 can be a plurality of top layer openings. The top layer openings 41 are formed in the waterproof top layer 40 in a mutually spaced manner to respectively correspond to the electrode pads 11. The central portion of each of the electrode pads 11 projects through respective top layer opening 41. The bottom surface of the waterproof top layer 40 is in tight engagement with the top surface of the waterproof base layer 20 so that each of the first receiving compartments S1 forms an independent wet keeping space.

Figure 5:
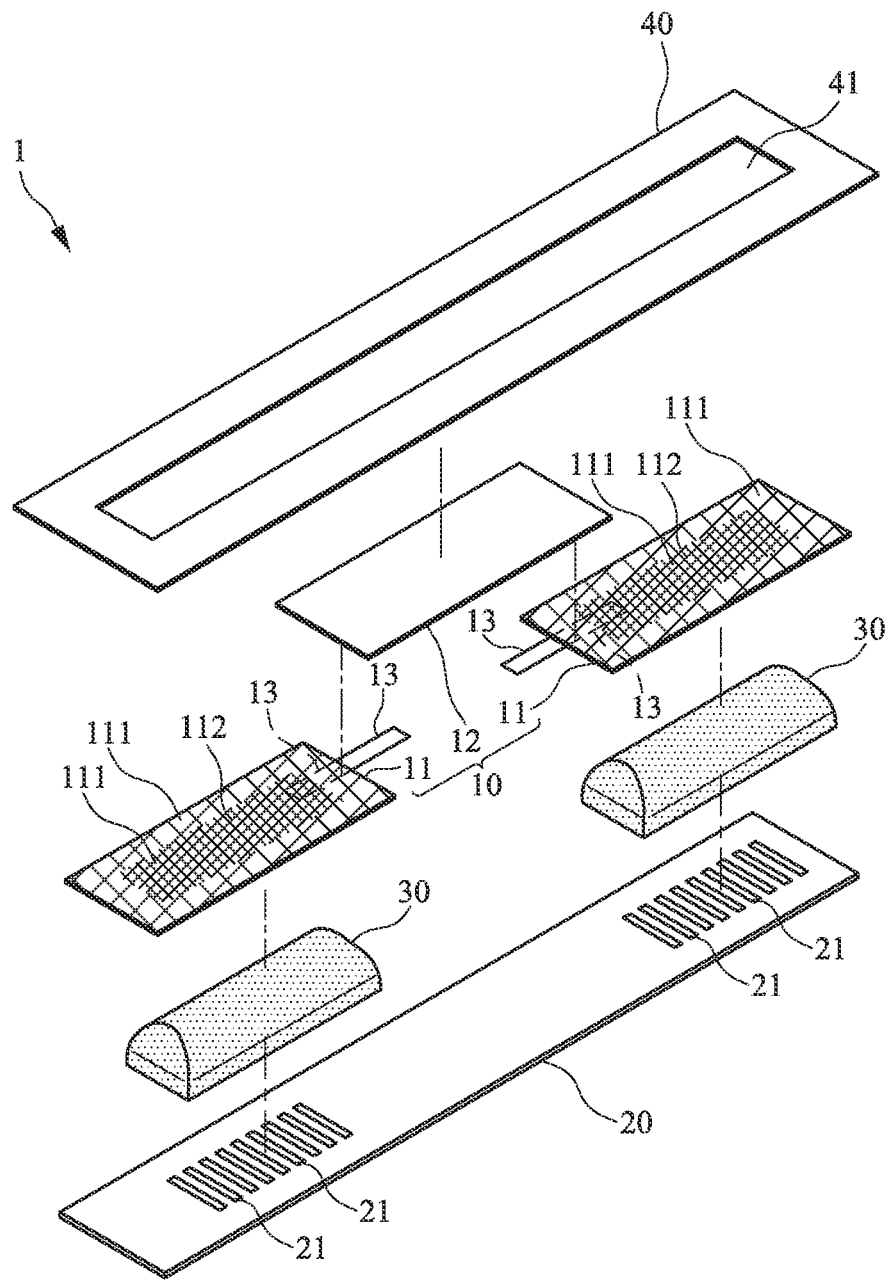
FIG. 5 is an exploded view showing that the physiological signal detection device of FIG. 1 comprises a waterproof top layer that forms a single top layer opening, waterproof connection bands are provided between electrode pads, and each electrode pad is provided with an extension conductor.

However, when the waterproof top layer 40 is embodied with a single top layer opening 41, as shown in FIGS. 4 and 5, at least one waterproof connection band 12 is connected between any two adjacent ones of the electrode pads 11. The waterproof connection band 12 is made of a thermoplastic material or a non-thermoplastic material. If the waterproof connection band 12 is made of a non-thermoplastic material, then at least one second receiving compartment S2 is formed between the waterproof connection band 12 and the waterproof base layer 20. The electrode pads 11 and the waterproof connection band 12 are jointed together to form a counterpart layer 10 that corresponds in shape to the waterproof base layer 20. The central portion of each electrode pad 11 of the counterpart layer 10 projects through the corresponding top layer opening 41. In this way, being assisted by the waterproof connection band 12, the electrode pads 11 can be efficiently attached to opposite sides of a specific portion of human body (such as left and right sides of head, left and right side parts of back, or opposite portions of chest and back of a heart-associated portion) and avoid short-circuit caused by mutual contact occurring between the electrode pads 11. Further, the second receiving compartment S2 functions to receive and retain other objects (such as electrical wires, sensors, and controllers). In case that no article or object is received in the second receiving compartment S2, the waterproof connection band 12 is bonded to the top surface of the base layer 20.

Further, for an electrode pad 11 of a relatively large size, to save expense and to effectively form electrical engagement between the electrode pad 11 and body surface, as shown in FIGS. 4 and 5, each of the electrode pads 11 is provided with at least one extension conductor 13 (which is particularly shown in the enlarged view at left lower corner of FIG. 4) connected thereto. The extension conductor 13 has an end extending into and electrically connected to the electrode pad 11 (namely being electrically connected to the conductive zone 112) and the extension conductor 13 has an opposite end projecting beyond an end of the electrode pad 11, whereby after each water absorption unit 30 absorbs water and bulges, each electrode pad 11 is set in a projecting condition so that easy electrical connection of the extension conductor 13 of the electrode pad 11 can be made with electrical current of the surface of human body. In a practical application, where the present invention is embodied with a single electrode pad 11, the extension conductor 13 discussed above can also be included. Further, when the present invention is embodied with more than two electrode pads 11, based on the sizes thereof, the electrode pads 11 can be selectively provided with and coupled to extension conductors 13.

The extension conductor 13 discussed above for the electrode pad 11 is formed by composing a plurality of conductive yarns that are provided for weaving purposes and are relatively flexible. The extension conductor 13 is electrically connected to an electrical wire (not shown), which has an opposite end electrically connected to physiological detection equipment (not shown), whereby electrical current of body surface flows through the electrode pad 11, the extension conductor 13, and the electrical wire to enter the physiological detection equipment. In a practical application, the extension conductor 13 is not a necessary component and the electrode pad 11 is directly and electrically connected to the electrical wire (not shown).

Figure 12:
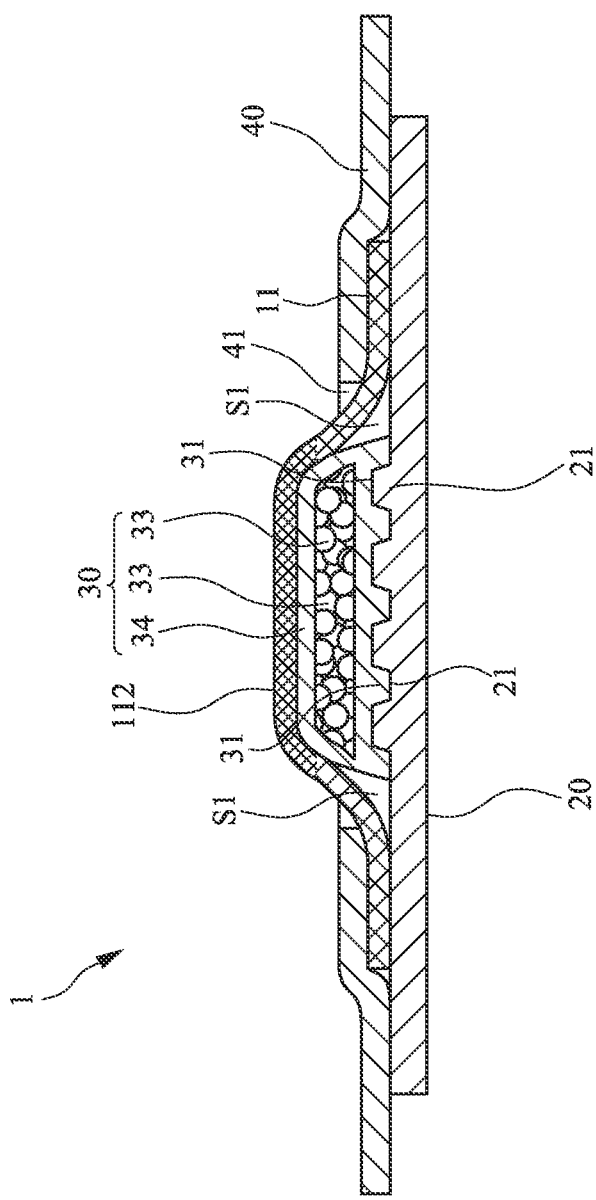
FIG. 12 is a cross-sectional view showing an embodiment comprising a water absorption unit according to the present invention that is composed of a water-preservation inner lining in combination with an accommodation sack.

Further, as shown in FIG. 12, the water absorption unit 30 may further comprise at least one water-preservation inner lining 33 and an accommodation sack 34 enclosing the water-preservation inner lining 33 in order to prevent fast loss of water. In an embodiment where a plurality of water-preservation inner linings 33 is included, to prevent a loose arrangement of the plurality of water-preservation inner linings 33, the accommodation sack 34 is used to enclose and confine the water-preservation inner linings 33 so that the water absorption unit 30 forms a structure that is adjustable and supports the electrode pad 11, this featuring both water preservation and supporting. When the present invention is attached to the human body surface, the water absorption unit 30 tightly abut against the corresponding electrode pad 11 to comply with and tightly engage with the curves of body surface, eliminating any potential gap therebetween, whereby electrical current on the body surface can be easily conducted to the electrode pad 11 to enhance the detection of variation of physiological signal.

The accommodation sack 34 has a bottom that is also provided with a plurality of spaced anti-skidding sections 31 and the top surface of the waterproof base layer 20 forms a plurality of spaced counterpart anti-skidding sections 21. The counterpart anti-skidding sections 21 respectively correspond to the anti-skidding sections 31. The counterpart anti-skidding sections 21 are respectively engageable with the anti-skidding sections 31 so as to prevent uneven raised configuration on an outside surface of the electrode pad 11 due to sliding of the water absorption unit 30.

Figure 13:
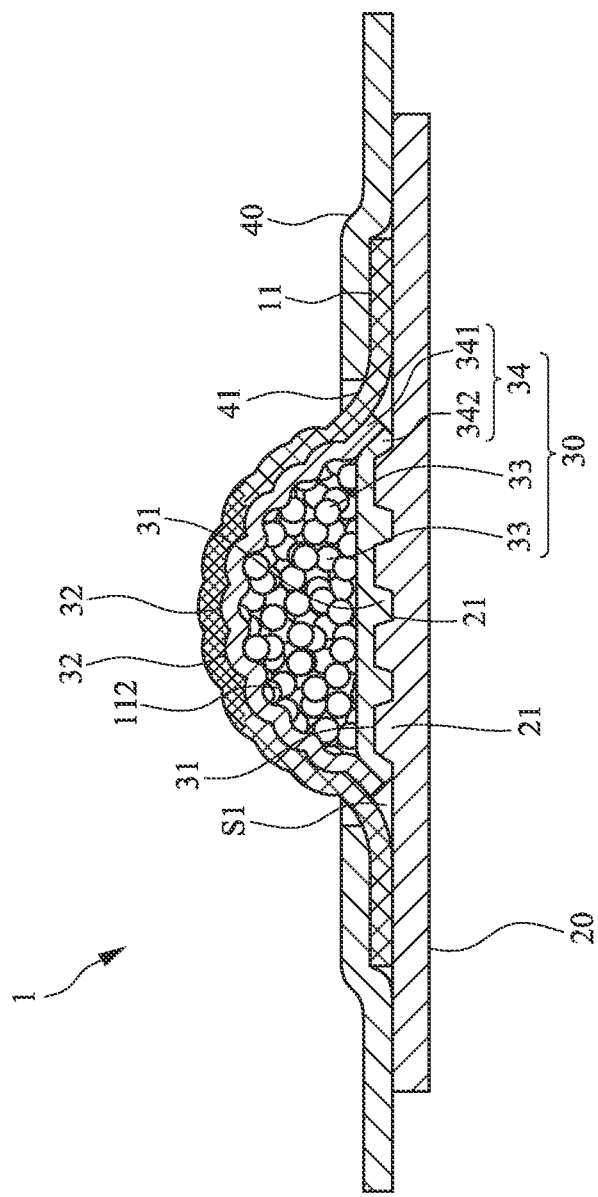
FIG. 13 is a cross-sectional view showing the accommodation sack of FIG. 12 comprises an upper water-penetrating layer and a lower water-proof layer that overlap each other and the water absorption unit absorbing water and getting bulging to show a projecting form.

To prevent the water of the water absorption unit 30 from being fast lost and to enhance wetting of the electrode pad 11 by the water absorption unit 30, as shown in FIG. 13, the accommodation sack 34 comprises an upper water-penetrating layer 341 and a lower water-proof layer 342 that overlap each other. The lower water-proof layer 342 is set in engagement with the waterproof base layer 20 and the upper water-penetrating layer 341 is in engagement with the electrode pad 11. The plurality of anti-skidding sections 31 is formed on a bottom surface of the lower water-proof layer 342. The upper water-penetrating layer 341 is a fabric layer, paper layer, or semi-permeable membrane resin layer. As such, water is only allowed to discharge through the accommodation sack 34' and the electrode pad 11 and this facilitates keeping water in the accommodation sack 34.

The water-preservation inner lining 33 is a component made of cotton paper, cotton fabric, silica gel, water-absorbing foam, fluff paste, sodium polyacrylate or other polymers of propenoic acid that show an equivalent function, or super-absorbent polymers. The shape of the component can be variable forms (such as sphere).

In the above discussion, the water absorption unit 30 has a top that is directly shaped as a projecting form (as shown in FIG. 7) and after absorbing water, the water absorption unit 30 bulges and shows a more distinctly projecting form to directly support the electrode pad 11. As shown in FIG. 13, if the water absorption unit 30 is made in the form comprising a plurality of water-preservation inner linings 33 in combination with an accommodation sack 34, then the water-preservation inner linings 33, after absorbing water, become bulging to make a plurality of projecting portions 32 on the surface of the accommodation sack 34. Such projecting portions 32 are also capable of supporting the corresponding electrode pad 11 and this makes it more compliant to the curves of body surface for more tight engagement.

As such, the present invention provides a physiological signal detection device, which comprises a combined structure of at least one electrode pad 11, a waterproof base layer 20, at least one water absorption unit 30, and at least one waterproof top layer 40 to provide water absorbing and wet keeping functions and additional functions of preventing water from fast loss through evaporation and preventing invasion of external liquid to affect conduction of electrical current and thus reducing interference of noise so as to facilitate the water absorption unit 30 wetting the electrode pad 11. Further, the water absorption unit 30 is capable of bulging by absorbing water to show a projecting form, so that an effect of easy contact and tight engagement of the electrode pad with human body surface is achieved to ease the detection of physiological signal of an inspection subject and improve convenience of use. Further, thermoplastic bonding layers (such as first bonding layer 60 and the second bonding layer 70) are included to facilitates bonding and also provides an effect of positioning whereby proper alignment of the water absorption unit 30 with respect tot the electrode pad 11 is enhanced and sliding is prevented so as to not affect the performance of conduction of electrical current.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A waterproof physiological signal detection device, comprising: a waterproof base layer; at least one electrode pad, which is positioned on a top surface of the waterproof base layer, the at least one electrode pad and the waterproof base layer forming a first receiving compartment therebetween; at least one water absorption unit, which is positioned in the first receiving compartment, the water absorption unit having a top engaging the electrode pad, the water absorption unit having a bottom engaging the waterproof base layer; and a waterproof top layer, which is positioned to overlap the top surface of the waterproof base layer, the waterproof top layer forming at least one top layer opening, the at least one top layer opening corresponding to and exposing the at least one electrode pad, an undersurface of a circumference of the top layer opening overlapping a circumference of a top surface of the electrode pad, the electrode pad having a central portion projecting through the top layer opening; wherein the water absorption unit forms in a bottom thereof a plurality of spaced anti-skidding sections, the waterproof base layer forming, in the top surface thereof, a plurality of spaced counterpart anti-skidding sections, the counterpart anti-skidding sections respectively corresponding to the anti-skidding sections, the counterpart anti-skidding sections being respectively engageable with the anti-skidding sections, and wherein the anti-skidding sections and the counterpart anti-skidding sections are defined by grooves or ribs.

2. The waterproof physiological signal detection device as claimed in claim 1, wherein the electrode pad is formed by weaving a plurality of non-conductive fibrous yarns and a plurality of conductive fibrous yarns, the plurality of conductive fibrous yarns of the electrode pad being woven to form a conductive zone.

3. The waterproof physiological signal detection device as claimed in claim 1, wherein the electrode pad is entirely made by weaving a plurality of conductive fibrous yarns.

4. The waterproof physiological signal detection device as claimed in claim 1, wherein the water absorption unit comprises one of cotton paper, cotton fabric, silica gel, and water-absorbing foam.

5. The waterproof physiological signal detection device as claimed in claim 1, wherein the water absorption unit comprises a component made of sodium polyacrylate.

6. The waterproof physiological signal detection device as claimed in claim 1, wherein the water absorption unit comprises an elastic object.

7. The waterproof physiological signal detection device as claimed in claim 1, wherein the waterproof base layer comprises a water-resistant upper layer and a fabric lower layer that overlap each other, the water-resistant upper layer being set in engagement with the water absorption unit.

8. The waterproof physiological signal detection device as claimed in claim 1, wherein the waterproof top layer comprises a fabric upper layer and a water-resistant lower layer that overlap each other, the top layer opening penetrating through the fabric upper layer and the water-resistant lower layer to expose the electrode pad, the water-resistant lower layer being set overlapping the top surface of the waterproof base layer.

9. The waterproof physiological signal detection device as claimed in claim 1 further comprises a first bonding layer, which overlaps a bottom surface of the waterproof top layer, the first bonding layer forming a bonding layer opening that corresponds to the at least one top layer opening, an undersurface of a circumference of the bonding layer opening overlapping a circumference of the top surface of the electrode pad, the central portion of the electrode pad projecting through the bonding layer opening and the top layer opening.

10. The waterproof physiological signal detection device as claimed in claim 9, wherein the first bonding layer comprises one of hot melt glue, adhesive, and adhesive tape.

11. The waterproof physiological signal detection device as claimed in claim 1, wherein the first bonding layer comprises one of hot melt glue, adhesive, and adhesive tape.

12. The waterproof physiological signal detection device as claimed in claim 1 further comprising a second bonding layer that overlaps a bottom surface of the waterproof base layer.

13. The waterproof physiological signal detection device as claimed in claim 12, wherein the second bonding layer comprises one of hot melt glue, adhesive, and adhesive tape.

14. The waterproof physiological signal detection device as claimed in claim 1, wherein the at least one electrode pad includes a plurality of electrode pads, which are arranged, in a mutually spaced manner, on the top surface of the waterproof base layer, each of the electrode pads and the waterproof base layer forming therebetween a first receiving compartment, the at least one water absorption unit including a plurality of water absorption units, each of the water absorption units being positioned in each of the first receiving compartments, each of the water absorption units having a top engaging each of the electrode pads, each of the water absorption units having a bottom engaging the waterproof base layer, the at least one top layer opening of the waterproof top layer including a plurality of top layer openings, which is formed in the waterproof top layer in a mutually spaced manner to respectively correspond to the electrode pads with the central portions of the electrode pads respectively projecting through the top layer openings.

15. The waterproof physiological signal detection device as claimed in claim 1, wherein the at least one electrode pad includes a plurality of electrode pads, which are arranged, in a mutually spaced manner, on the top surface of the waterproof base layer, each of the electrode pads and the waterproof base layer forming therebetween a first receiving compartment, the at least one water absorption unit including a plurality of water absorption units, each of the water absorption units being positioned in each of the first receiving compartments, each of the water absorption units having a top engaging each of the electrode pads, each of the water absorption units having a bottom engaging the waterproof base layer, a waterproof connection band being connected to two adjacent ones of the electrode pads, the waterproof connection band and the waterproof base layer forming therebetween a second receiving compartment, the electrode pads and the waterproof connection band being connected to each other to form a counterpart player corresponding in shape to the waterproof base layer, the central portions of the electrode pads of the counterpart layer respectively projecting through the top layer openings.

16. The waterproof physiological signal detection device as claimed in claim 9, wherein each of the electrode pads is further provided with at least one extension conductor, which has an end extending into and electrically with each of the electrode pads and an opposite end extending beyond one side of each of the electrode pads.

17. The waterproof physiological signal detection device as claimed in claim 1, wherein the water absorption unit comprises at least one water-preservation inner lining and an accommodation sack enclosing the water-preservation inner lining, the accommodation sack having a bottom forming a plurality of spaced anti-skidding sections, the top surface of the waterproof base layer forming a plurality of spaced counterpart anti-skidding sections, the counterpart anti-skidding sections respectively corresponding to the anti-skidding sections, the counterpart anti-skidding sections being respectively engageable with the anti-skidding sections.

18. The waterproof physiological signal detection device as claimed in claim 17, wherein the water-preservation inner lining comprises one of cotton paper, cotton fabric, silica gel, and water-absorbing foam.

19. The waterproof physiological signal detection device as claimed in claim 17, wherein the water-preservation inner lining comprises a component made of sodium polyacrylate.

20. The waterproof physiological signal detection device as claimed in claim 17, wherein the accommodation sack comprises an upper water-penetrating layer and a lower water-proof layer that overlap each other, the lower waterproof layer being set in engagement with the waterproof base layer, the upper water-penetrating layer being set in engagement with the electrode pad, the plurality of anti-skidding sections being formed on a bottom surface of the lower waterproof layer.

21. The waterproof physiological signal detection device as claimed in claim 20, wherein the upper water-penetrating layer comprises one of a fabric layer, a paper layer, or a semi-permeable membrane resin layer.

22. The waterproof physiological signal detection device as claimed in claim 1, wherein the water absorption unit shows a projecting form.

* * * * *